(12) United States Patent
Cannon

(10) Patent No.: US 7,021,312 B2
(45) Date of Patent: Apr. 4, 2006

(54) ASSISTED BREATHING DEVICE AND METHOD OF WEARING SAME

(76) Inventor: James L. Cannon, 5297 Cleveland Hwy., Clermont, GA (US) 30527

( * ) Notice: Subject to any disclaimer, the term of this patent is extended or adjusted under 35 U.S.C. 154(b) by 0 days.

(21) Appl. No.: 10/886,931

(22) Filed: Jul. 8, 2004

(65) Prior Publication Data
US 2006/0005840 A1    Jan. 12, 2006

(51) Int. Cl.
A62B 18/08 (2006.01)
(52) U.S. Cl. ............. 128/206.29; 128/207.11; 128/207.13; 128/848
(58) Field of Classification Search ......... 128/207.18, 128/207.13, 207.17, 206.27, 206.21, 205.25, 128/204.12, 200.24, 201.26, 206.29, 848
See application file for complete search history.

(56) References Cited

U.S. PATENT DOCUMENTS

| | | | | |
|---|---|---|---|---|
| 5,752,510 A | * | 5/1998 | Goldstein | 128/207.18 |
| 5,755,219 A | * | 5/1998 | Thornton | 128/201.18 |
| 5,829,441 A | * | 11/1998 | Kidd et al. | 128/848 |
| 5,954,048 A | * | 9/1999 | Thornton | 128/201.18 |
| 5,983,892 A | * | 11/1999 | Thornton | 128/201.26 |
| 6,012,455 A | * | 1/2000 | Goldstein | 128/207.18 |
| 6,209,542 B1 | * | 4/2001 | Thornton | 128/206.29 |
| 6,371,112 B1 | * | 4/2002 | Bibi | 128/204.18 |
| 6,571,798 B1 | * | 6/2003 | Thornton | 128/206.21 |
| 6,789,543 B1 | * | 9/2004 | Cannon | 128/207.18 |

\* cited by examiner

Primary Examiner—Mital Patel
(74) Attorney, Agent, or Firm—Kilpatrick Stockton LLP

(57) ABSTRACT

There is disclosed an improved breathing assistance device. The breathing assistance device comprises a nasal mask, an upper mouth piece and a frame attached to the upper mouth piece. The frame is coupled to the nasal mask such that orbital movement of the nasal mask is permitted while air under pressure is supplied to the nasal mask through the coupling. A method of using a breathing assistance device is also disclosed.

22 Claims, 4 Drawing Sheets

ASSISTED BREATHING DEVICE AND METHOD OF WEARING SAME

FIELD OF THE INVENTION

The present invention relates to a device for improving the breathing of the user during sleep. Specifically, the device relates to a nasal mask, an upper mouth piece and a frame that maintains the proper seating of the nasal mask during sleep, resulting in a more efficient treatment of breathing disorders.

BACKGROUND OF THE INVENTION

The present invention relates to an improved breathing device for delivering air under pressure to nasal passages in the treatment of breathing disorders, such as sleep apnea, ventilation difficulties or anesthetic gas administration. Sleep related breathing disorders adversely affect the breathing of individuals during periods of sleep. Sleep related breathing disorders include difficulties in sleeping, snoring, and more serious conditions, such as sleep apnea. Sleep apnea is the temporary cessation of breathing during sleep. Persons suffering from sleep apnea can stop breathing for periods as short as a few seconds, to as long as several minutes. Sleep apnea is a common disorder, affecting about a quarter of all middle-aged men in the United States, and about ten percent of middle-aged women. There are several forms of sleep apnea, including obstructive sleep apnea, central sleep apnea and mixed sleep apnea. Obstructive sleep apnea results when the flow of air in and out of the airways is blocked by upper airway obstruction. This form of sleep apnea is marked by loud snorting, snoring and gasping sounds during sleep. Central sleep apnea is caused by the absence of respiratory muscle activity. Persons suffering from this sleep apnea may exhibit excessive daytime sleepiness. Mixed apnea begins with the absence of respiratory effort and is followed by upper airway obstruction. Prolonged sleep apnea can result in headache, fatigue, and drowsiness. Other disorders include nighttime thrashing, sleepwalking, enuresis, disorientation, personality changes, intellectual deterioration, sexual dysfunction, and hypnagogic hallucinations.

Typically sleep apnea is treated by Continuous Positive Air Pressure (CPAP). For such therapy a device that forces air into an individual's air passageway to affect a slightly positive pressure of air to the nasal passages. The application of a slightly positive pressure of air is typically effective in reversing airway obstruction in patients suffering from obstructive sleep apnea.

Typically, a person suffering from sleep apnea must use CPAP therapy on a regular basis to prevent the reoccurrence of the sleep disorder. The patient typically wears a mask-like device that is connected to a CPAP device that provides an elevated or slightly positive air pressure into a patient's upper air passageway. Problems associated with wearing existing masks during periods of sleep are sufficient to deter many patients from continuing CPAP therapy. The most common problem associated with CPAP mask systems in use today is loss of the air seal between the mask and the user's face. This results in a loss in pressure, and, thereby, jeopardizes the effectiveness of the CPAP therapy. If the user is asleep and unaware of the escaping air, severe burns can occur to the skin. If the stream of pressurized air happens to be directed toward an eye, severe burns to the eyelid and surrounding tissue may occur, resulting in the eye being swollen shut.

Adjustable straps are commonly used to secure the mask to the patient's face. The straps are usually made from an elastic material. There are usually two to three straps attached to the mask. It is frequently difficult to adjust the straps sufficiently so as to hold the mask in the proper position on the user's face. The more straps attached to the mask, the harder it is to properly adjust them so that they are in equilibrium. In an attempt by the user to adjust the straps so as to hold the mask in place during movements that occur during a full night of sleep, the straps are pulled so tightly that the mask becomes very uncomfortable. The excessive pressure exerted by the mask usually causes red areas on the face and sometimes even causes blisters. Heavy pressure is not only uncomfortable, but actually distorts the elastomeric portion of the mask that makes contact with the user's face making it more difficult to maintain an air seal.

Various designs have been proposed to overcome some of these problems. See for example U.S. Pat. Nos. 6,012,455; 6,192,886; 6,209,542; 6,244,865; 6,305,379; 6,341,060 and 6,374,824; (the disclosures of which are incorporated herein by reference). However, these devices are not entirely satisfactory. The problems with improperly fitting masks are so severe that typically 50 percent of people who try CPAP therapy reject it.

Accordingly, there is a need for a device that permits a stable seating of a breathing device during the treatment of a breathing disorder that is also comfortable to wear during periods of sleep. This in turn will result in more effective treatment of breathing disorders, such as sleep apnea.

SUMMARY OF THE INVENTION

The present invention satisfies the above-described needs by providing an improved breathing device. The breathing device of the present invention comprises a nasal mask and an upper mouth piece that is attached to a frame. A coupling is provided between the frame and nasal mask such that air under pressure is provided to the nasal mask through the coupling while the coupling permits orbital movement of the nasal mask. The coupling also prevents the nasal mask from moving away from a wearer's face. Thereby, the nasal mask can be held in place with a more stable controlled force than can be achieved with the strap systems associated with the prior art. The coupling allows for moderate rotational and pivotal movement (orbital movement) of the mask resulting from movement of the wearer's head without losing the air seal. When the frame contacts the nasal mask through the centrally located coupling, the force is equally distributed around the periphery of the mask, thus avoiding the pressure points on a wearer's face associated with prior art nasal mask systems. Also, the absence of air hoses or straps attached to the nasal mask avoids the dislodging forces associated with the prior art breathing devices.

Accordingly, it is an object of the present invention to provide an improved breathing device.

Another object of the present invention is to provide a nasal mask and frame system that permits orbital movement of the nasal mask.

A further object of the present invention is to provide a nasal mask that is comfortable to wear.

Another object of the present invention is to provide a nasal mask that does not easily become unseated on a wearer's face during periods of sleep, thereby losing the air seal between the mask and the wearer's face.

Yet another object of the present invention is to provide a nasal mask that can be worn without air hoses or straps attach to the nasal mask.

These and other objects, features and advantages of the present invention will become apparent upon reviewing the following detailed description of the disclosed embodiments and the appended drawing and claims.

DETAILED DESCRIPTION OF THE DRAWINGS

Figure 1:
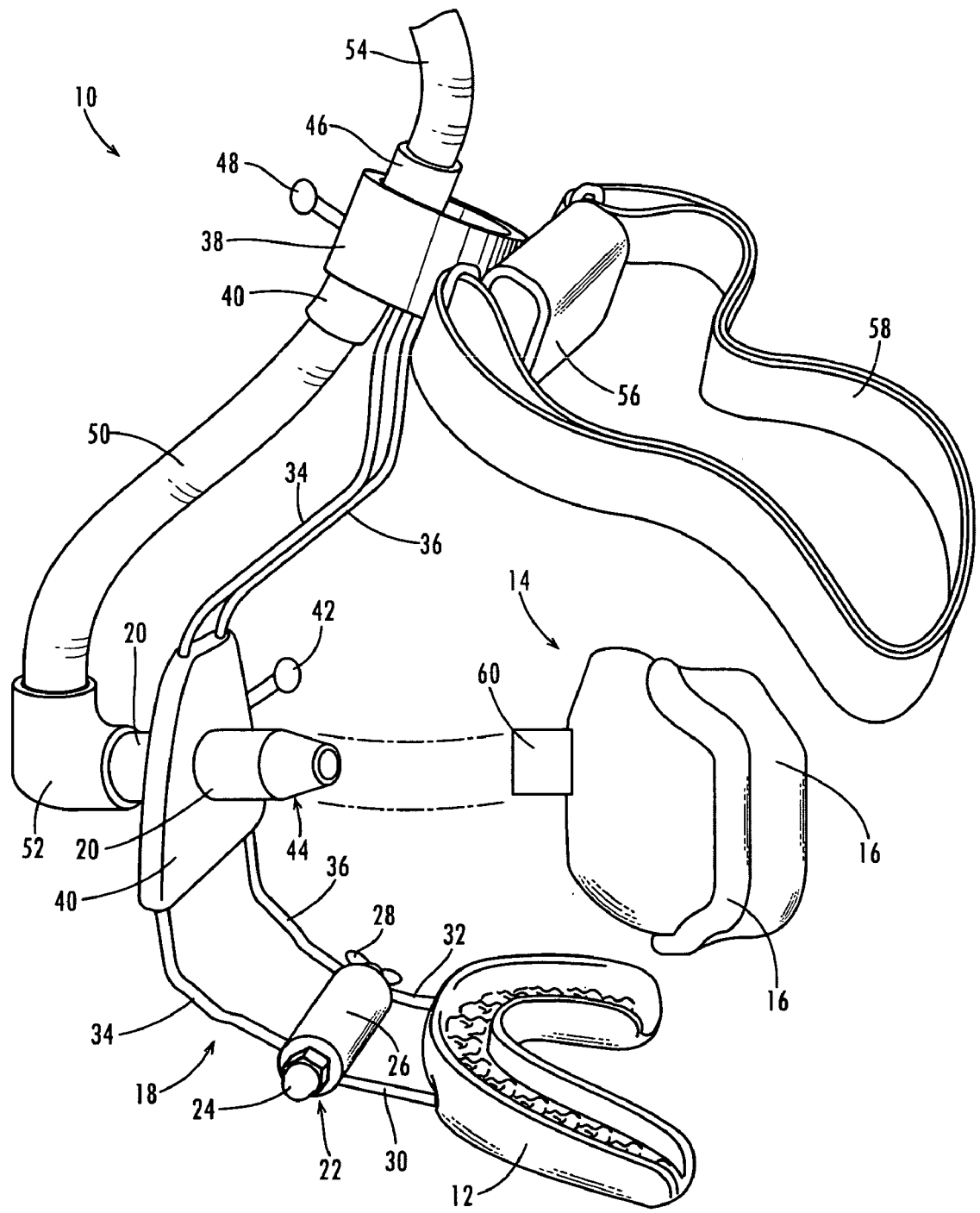
FIG. 1 is a partially exploded perspective view of a disclosed embodiment of the breathing device of the present invention.

With reference to the drawing in which like numbers indicate like elements throughout the several views, there will be seen that there is a breathing assistance device 10. The breathing assistance device 10 comprises a dental appliance comprising an upper mouth piece 12 (FIG. 1) adapted to receive at least some of a user's upper teeth. The upper mouth piece 12 is preferably custom made to fit a user's teeth so that the mouth piece fits properly and is comfortable to wear. The upper mouth piece 12 is made from a composite material, or other suitable materials, typically used for dental appliances, such as dental splints, and is well know to those skilled in the art. The breathing assistance device 10 also comprises a nasal mask 14, such as for providing CPAP treatment. The nasal mask 14 include a skirt 16 that provides an air seal when properly positioned on a wearer's face (not shown).

Attached to the upper mouth piece 12 is a frame 18. The frame 18 comprises a wire structure 30, 32, 34, 36 for supporting a first fitting 20 for providing air under pressure to the nasal mask 14. The wires 30–36 of the frame 18 are preferably made from a relatively heavy gauge stainless steel, such as 0.072 to 0.075 gauge. A hinge 22 comprising a bolt 24 upon which is disposed a plastic cylindrical spacer 26 is provided on the frame 18. A wing nut 28 is threaded on the end of the bolt 24. The wires 30, 32 on the ends opposite the upper mouth piece 12 are formed into loops so that the bolt 24 can pass therethrough. The loop ends of the wires 30, 32 are therefore rotatable on the bolt 24.

The frame 18 also comprises a pair of wires 34, 36. The wires 34, 36 are preferably made from the same material as the wires 30, 32. The wires 34, 36 are attached at one end to an annular collar 38 and at the other end to the hinge 22. The wires 34, 36 on the ends opposite the collar 38 are formed into loops so that the bolt 24 can pass therethrough and the loop ends of the wires are rotatable on the bolt.

The hinge 22 is assembled by inserting the bolt 24 through the loop end of the wire 30, the loop end of the wire 34, the spacer 26, the loop end of the wire 36 and the loop end of the wire 32. Then, the wing nut 28 is threaded onto the end of the bolt 24. It will be appreciated that when the wing nut 28 is relatively loose, the wires 30, 32 and 34, 36 are free to rotate about the bolt 24. However, when the wing nut 28 is tightened on the bolt 24, the loop ends of the wires 30, 34 are captured between the bolt head and the spaces 26 and the loop ends of the wires 32, 36 are captured between the spaces and the wing nut such that the wires are no longer free to rotate on the bolt. Thus, by selectively loosening and tightening the wing nut 28, the angle formed between the wires 30, 32 and the wires 34, 36 can be adjusted.

While the frame 18 useful in the present invention has been illustrated as being formed from wires 30–36, it is specifically contemplated that the frame may be made from other materials, such as plastic, and that the frame can be made as a solid structure, instead of wires. Thus, the frame can be made from any suitable, rigid material and in any suitable structure, shape or conformation as long as it is capable of supporting the upper mouth piece 12, first fitting 20 and collar 38 in their relative spaced relationships.

Mounted on the wires 34, 36 intermediate their ends is a plastic bridge 40. The bridge 40 provides stability to the wires 34, 36 and also provides support for the first fitting 20. The bridge 40 is also selectively slideable on the wires 34, 36 in a vertical direction. A set screw 42 is provided for locking the bridge 40 at a desired position on the frame 18.

The first fitting 20 comprises a hollow tube having a tapered portion 44 adjacent the end thereof that faces the nasal mask 14. The tapered portion 44 of the first fitting 20 reduces the outside diameter of the tube from its diameter at the end opposite the tapered portion to approximately one-half of the original diameter at the end of the tapered portion. The first fitting 20 is annular in cross-section so that air under pressure may freely flow there through. The first fitting 20 is preferably made from a rigid material, such as rigid, plastics, for example CPVC; ceramics; stainless steel and the like. It is also contemplated that the first fitting 20 may desirably be made from non-flexible, but resilient materials, such as resilient plastics, for example polyethylene, silicone rubber, and the like.

The collar 38 is sized and shaped so that a 45° CPVC elbow 46 can pass there through. The collar 38 includes a set screw 48 for securing the elbow 46 therein. One end of the elbow 38 includes a nipple (not shown) for attaching a flexible plastic air hose 50 thereto. The opposite end of the air hose 50 is attached to a 90° CPVC elbow 52. The opposite end of the CPVC elbow 52 is connected to the non-tapered end of the first fitting 20. The end of the elbow 46 opposite the hose 50 is connected to a flexible plastic air hose 54. The end of the air hose 54 opposite the elbow 46 is connected to a CPAP device (not show). Thus, air under positive pressure may freely flow from the CPAP device, through the hose 54, the elbow 46, the hose 50, the elbow 52 and the first fitting 20.

The wires 34, 36 may contain bends so as to position the bridge 40 substantially vertically. The wires 34, 36 may also contain additional bends so that the collar 38 is positioned above the nasal mask 14 and the first fitting 20 is spaced away from the wearer's nose (not shown).

The collar 38 also includes a cushion pad 56 attached thereto for contacting a wearer's forehead (not shown) to make the breathing apparatus 10 more comfortable to wear.

An adjustable elastic strap 58 is also attached to the collar 38 so that the end of the frame opposite the upper mouth piece 12 can be secured to a wearer's head (not shown).

Figure 2:
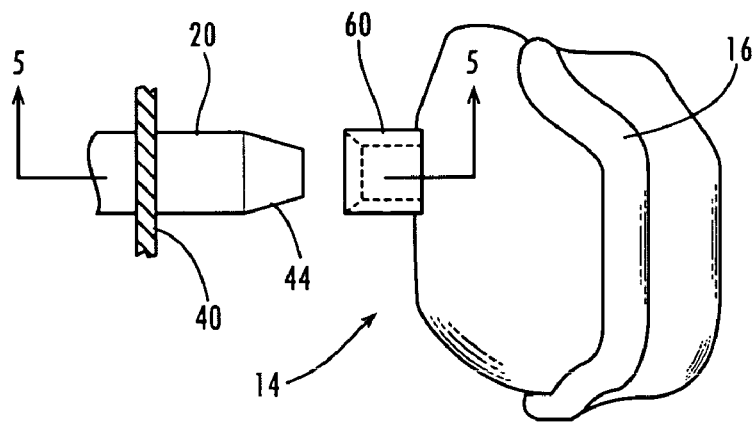
FIG. 2 is a side view of the nasal mask shown in FIG. 1.
Figure 3:
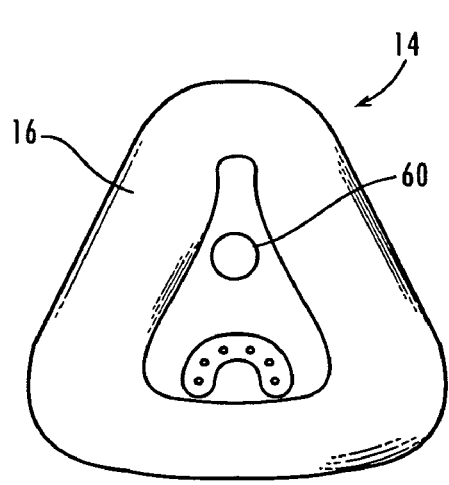
FIG. 3 is a rear view of the nasal mask shown in FIG. 1.
Figure 4:
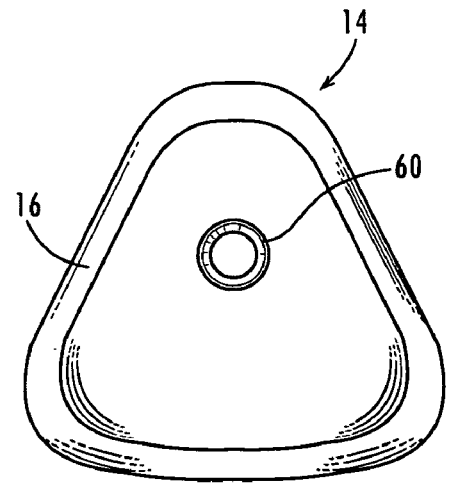
FIG. 4 is a front view of the nasal mask shown in FIG. 1.

The nasal mask 14 includes a second fitting 60. As can be seen in FIGS. 2–4, the second fitting is located approximately in the middle of the mask 14. The location of the second fitting 60 on the nasal mask 14 is determined by finding the location at which when pressure is applied to the mask at that point, the force would be distributed evenly on the sealing skirt 16 of the mask, an air seal would be established on the wearer's face and the mask would feel comfortable to the wearer.

Figure 5:
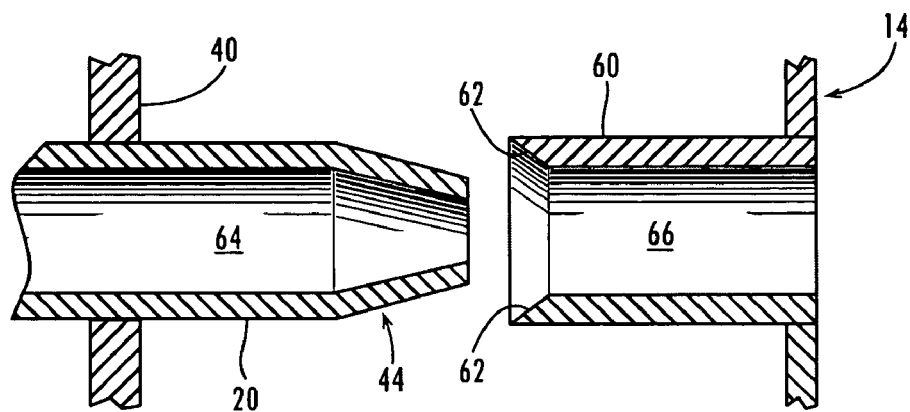
FIG. 5 is a cross-sectional view taken along the line 5—5 of the a portion of the nasal mask shown in FIG. 2.
Figure 6:
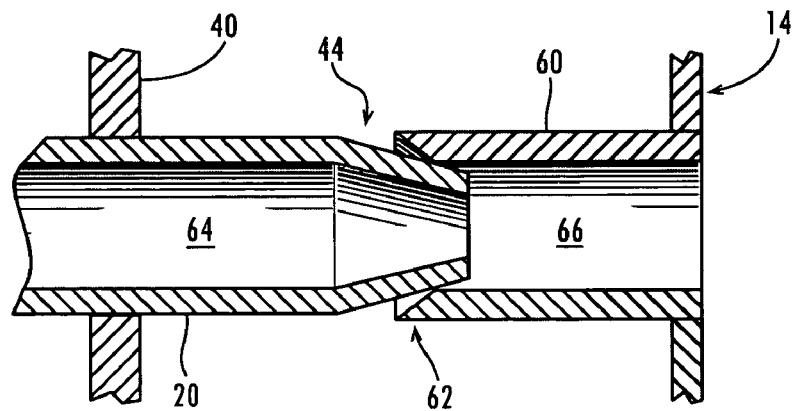
FIG. 6 is an alternate cross-sectional view of the portion of the nasal mask shown in FIG. 5, showing the fittings in a coaxial mating position.
Figure 7:
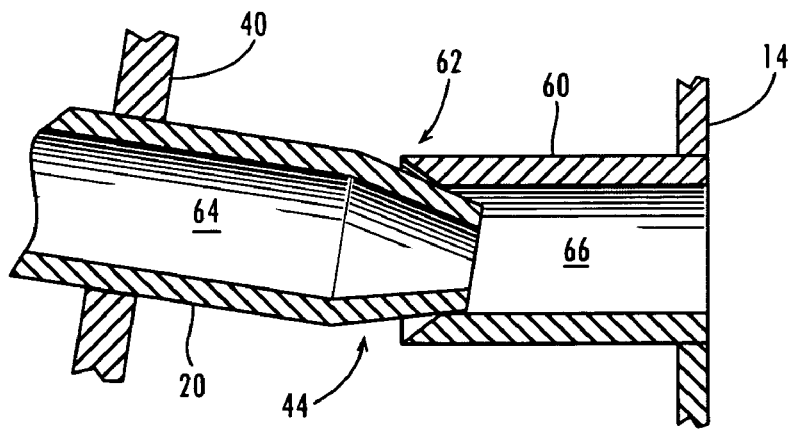
FIG. 7 is an alternate cross-sectional view of the portion of the nasal mask shown in FIG. 5, showing the fittings in a non-coaxial mating position.

With particular reference to FIGS. 5–7, it will be seen that the second fitting 60 includes a flared portion 62. This flared portion 62 is made by beveling the inside of the wall of second fitting 60 so that the inside diameter of the second fitting is greater in the flared portion than in the portion that is not flared. In FIGS. 6 and 7 it can be seen that the tapered portion 44 of the first fitting 20 and the flared portion 62 of the second fitting 60 permit the first fitting to mate with the second fitting. It will also be appreciated that when the first fitting 20 is mated with the second fitting 60, the outside of the tapered portion 44 fits snuggly against the inside of the flared portion 62 and provides a substantially air tight seal there between.

Since the first fitting 20 is a hollow tube, it defines a first air passageway 64 there through. Similarly, since the second fitting 60 is a hollow tube, it defines a second air passageway 66 there through. When the first fitting 20 is mated with the second fitting 60, the fittings provide a coupling of the first air passageway 64 to the second air passageway 66 thereby permitting air under positive pressure to freely flow through the fittings 20, 60 to the nasal mask 14.

It will also be appreciated that the substantially air tight seal between the first fitting 20 and the second fitting 60 is maintained even when the second fitting is not coaxially aligned with the first fitting. As is shown in FIG. 6, the first fitting 20 and the second fitting are in coaxial alignment.

However, due to natural movements of a wearer's head, such as may be experienced when rolling over, the nasal mask 14 may move relative to the frame 18. Such movement may result in the second fitting 60 being slightly misaligned; i.e., non-coaxial, with the first fitting 20. Such misalignment may be as little as a few degrees or as much as 10°–20° off coaxial. The nature of the coupling between the first fitting 20 and the second fitting 60 permits such misalignments without losing the air tight seal formed there between, as shown in FIG. 7.

Use of the breathing assistance device 10 will now be considered. The hose 54 is connected to a CPAP device (not shown). A patient in need of CPAP treatment inserts the upper mouth piece 12 into his mouth so that at least a few of his teeth fit into the upper mouth piece and the upper mouth piece is retained in the wearer's mouth. The nasal mask 14 is then placed over the patient's nose and seated against his face. The hinge 22 is adjusted by loosening or tightening the wing nut 28 so that the first fitting 20 mates with the second fitting 60. The set screw 42 may be adjusted so that the bridge 40 may be moved up or down to assure proper (i.e., axial) alignment of the first fitting 20 and the second fitting 60. The hinge 22 is also adjusted so that sufficient force is applied by the first fitting 20 to the second fitting 60 and hence the nasal mask 14, thereby pressing the nasal mask into contact with the wearer's face such that the nasal mask is retained on the wearer's face without the use of straps or other mask retaining apparatus. When the frame 18 is properly positioned, the wing nut 28 is tightened so that the frame is retained in the proper position. With the cushion pad 56 contacting the wearer's forehead, the strap 58 can then be placed around the patient's head so that the frame 18 is held in a relatively rigid, stable position relative to the patient's face.

It will be appreciated that the mask retaining force applied by the first fitting 20 to the second fitting 60 and hence to the nasal mask 14 is directed directly toward the wearer's face irrespective of the position of the wearer's head. Furthermore, the magnitude of the mask retaining force is substantially constant irrespective of the position of the wearer's head.

It will be further appreciated that since the nasal mask 14 is retained on a wearer's face by the first fitting 20 mating with the second fitting 60, the nasal mask may move moderately without becoming unseated on the wearer's face. Furthermore, movement of the wearer's head, such as rolling from side-to-side during sleep, will not disengage the first fitting 20 from the second fitting 60 and sufficient pressure will be applied to the nasal mask 14 to retain the mask on the wearer's face and maintain the pressure seal during normal sleep movements.

When CPAP treatment is no longer need, such as in the morning, the nasal mask 14 can be removed from the wearer's face by simple removing the strap 58 from the wearer's head and removing the upper mouth piece 12 from the wearer's mouth, thereby disengaging the first fitting 20 from the second fitting 60. The nasal mask 14 can then be removed from the wearer's face.

Figure 8:
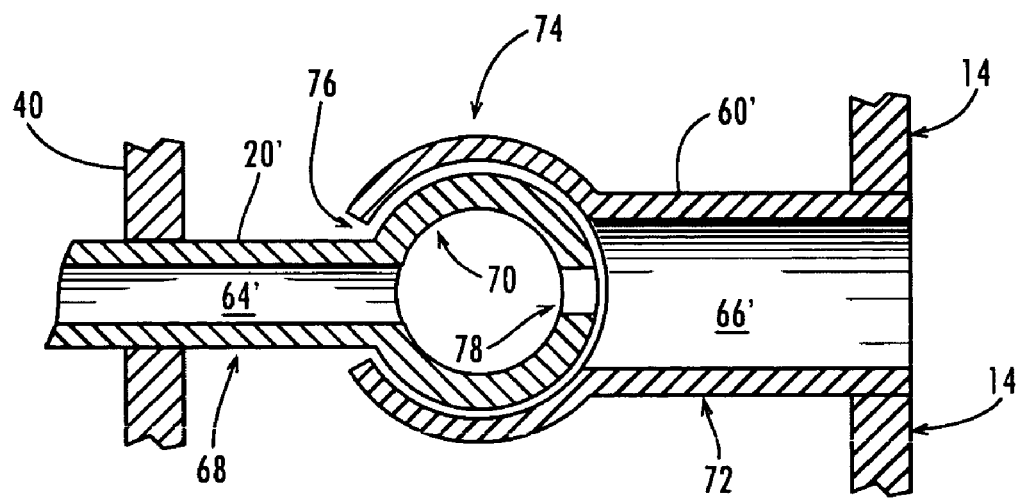
FIG. 8 is partial cross-sectional view an alternate disclosed embodiment of the breathing device of the present invention showing a ball-and-socket coupling between the nasal mask and the frame, showing the fittings in coaxial alignment.

With reference to FIG. 8, it will be seen that there is disclosed an alternate disclosed embodiment of the first and second fitting used in the present invention. The breathing assistance device for this alternate embodiment is identical to the breathing assistance device described above, except that the first and second fittings 20, 60 are replaced by fittings that form a ball-and-socket joint, as shown in FIG. 8. The ball-and-socket joint is formed by a first fitting 20' that is attached to the bridge 40 on the frame 18 and by a second fitting 60' that is attached to the nasal mask 14. The first fitting 20' includes a hollow tubular portion 68 and an enlarged spherical head portion 70. The second fitting 60' includes a hollow tubular portion 72 and an enlarged spherical head-receiving portion 74. The head-receiving portion 74 of the second fitting 60' defines an opening 76 that is slightly smaller than the diameter of the enlarged head portion 70 of the first fitting 20', but is larger than the tubular portion 68 of the first fitting. The enlarged head portion 70 of the first fitting 20' is therefore captured within the enlarged head-receiving portion 74 of the second fitting 60'. The dimensions of the enlarged head portion 70 and the enlarged head-receiving portion 74 are such that a substantially air tight seal is formed there between. Although the dimensions of the enlarged head portion 70 and the enlarged head-receiving portion 74 are such that an air tight seal is formed there between, the enlarged head portion is free to rotate within then head-receiving portion.

The first fitting 20' defines a first air passageway 64'. The enlarged head portion 70 of the first fitting 20' also defines an opening 78. The second fitting 60' defines a second air passageway 66'. Thus, when the first fitting 20' is coaxially aligned with the second fitting 60', as shown in FIG. 8, air is free to flow through the first air passageway 64', out the opening 78 in the enlarged head portion 44 and through the second air passageway 66' to the nasal mask 14.

Figure 9:
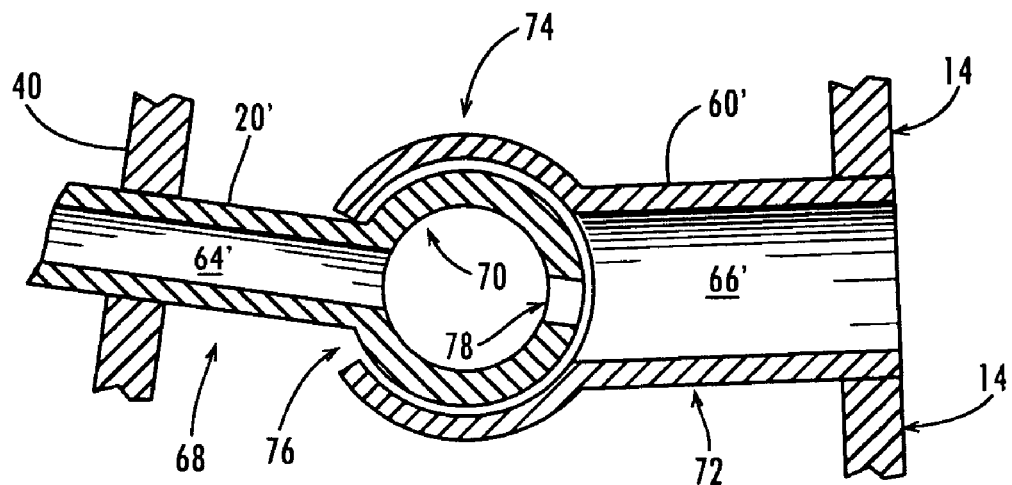
FIG. 9 is partial cross-sectional view an alternate disclosed embodiment of the breathing device of the present invention showing a ball-and-socket coupling between the nasal mask and the frame, showing the fittings in non-coaxial alignment.

It will also be appreciated that the substantially air tight seal between the first fitting 20' and the second fitting 60' is maintained even when the second fitting is not coaxially aligned with the first fitting, as is shown in FIG. 9. Due to natural movements of a wearer's head, such as may be experienced when rolling over during sleep, the nasal mask 14 may move relative to the frame 18. Such movement may result in the second fitting 60' being slightly misaligned; i.e., not coaxial, with the first fitting 20'. Such misalignment may be as little as a few degrees or as much as 10°–20° off coaxial. The nature of the coupling between the first fitting 20' and the second fitting 60' permits such misalignments without losing the air tight seal formed there between. Thus, when the first fitting 20' is coaxially aligned with the second fitting 60', as shown in FIG. 8, air is free to flow through the first air passage way 64', out the opening 78 in the enlarged head portion 44 and through the second air passageway 66' to the nasal mask 14. Furthermore, when the first fitting 20' is coaxially misaligned with the second fitting 60', as shown in FIG. 9, air is still free to flow through the first air passage way 64', out the opening 78 in the enlarged head portion 44 and through the second air passageway 66' to the nasal mask 14.

The movement that is possible with the ball-and-socket joint illustrated in FIGS. 8 and 9 is not limited to up and down or back and forth, but is continuously variable in combinations of both. This type of motion is known as orbital motion. This same type of motion is possible with the first and second fittings 20, 60 shown in FIGS. 5–7. Therefore, as used herein, the term "orbital motion" shall mean the type of motion that is possible for the second fitting 60 (and therefore the nasal mask 14) with respect to the first fitting 20 (and therefore with respect to the frame 18) in both the ball-and-socket configuration of FIGS. 8 and 9 and the configuration shown in FIGS. 5–7.

The assisted breathing device 10 using the ball-and-socket configuration is used in the same manner as the assisted breathing device described above using the coupling shown in FIGS. 5–7. Conveniently, the second fitting 60' may be made from plastic so that the enlarged head portion 70 of the first fitting 20' can be snapped into the enlarged head-receiving portion 74 of the second fitting. This permits a quick and easy method of attaching and disconnecting the nasal mask 14 from the frame 18.

Use of the breathing assistance device 10 using the ball-and-socket configuration of FIGS. 8 and 9 will now be considered. The hose 54 is connected to a CPAP device (not shown). If the nasal mask 14 is not connected to the frame 18, the enlarged head portion 70 of the first fitting 20' is pushed into the enlarged head-receiving portion 74 of the second fitting 60'. A patient in need of CPAP treatment inserts the upper mouth piece 12 into his mouth so that at least a few of his teeth fit into the upper mouth piece and the upper mouth piece is retained in the wearer's mouth. The nasal mask 14 is then placed over the patient's nose and seated against his face. The hinge 22 is adjusted by loosening or tightening the wing nut 28 so that the nasal mask fits comfortably on the patient's face. The set screw 42 may be adjusted so that the bridge 40 may be moved up or down to assure proper (i.e., coaxial) alignment of the first fitting 20' and the second fitting 60'. The hinge 22 is also adjusted so that sufficient force is applied by the first fitting 20' to the second fitting 60' and hence to the nasal mask 14, thereby pressing the nasal mask into contact with the wearer's face such that the nasal mask is retained on the wearer's face without the use of straps or other mask retaining apparatus. When the frame 18 is properly positioned, the wing nut 28 is tightened so that the frame is retained in the proper position. With the cushion pad 56 contacting the wearer's forehead, the strap 58 can then be placed around the patient's head so that the frame 18 is held in a relatively rigid, stable position relative to the patient's face.

It will be appreciated that the mask retaining force applied by the first fitting 20', to the second fitting 60' and hence to the nasal mask 14 is directed directly toward the wearer's face irrespective of the position of the wearer's head. Furthermore, the magnitude of the mask retaining force is substantially constant irrespective of the position of the wearer's head.

It will be further appreciated that since the nasal mask 14 is retained on a wearer's face by the first and second fittings 20', 60' forming a ball-and-socket joint, the nasal mask may move moderately without becoming unseated on the wearer's face. Furthermore, movement of the wearer's head, such as rolling from side-to-side during sleep, will not disengage the first fitting 20' from the second fitting 60' and sufficient pressure will be applied to the nasal mask 14 to retain the mask on the wearer's face and maintain the pressure seal during normal sleep movements.

When CPAP treatment is no longer need, such as in the morning, the assisted breathing device 10 can be removed from the wearer's face by loosening the head strap 58 and removing it from the wearer's head and simply removing the upper mouth piece 12 from the wearer's mouth. If its is desired to disconnect the nasal mask 14 from the frame 18, the enlarged head portion 70 of the first fitting 20' can be pulled from the enlarged head-receiving portion 74 of the second fitting 60'. Detaching the nasal mask 14 from the frame 18 permits the nasal mask to be cleaned and/or disinfected as necessary.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A breathing device comprising:
   a nasal mask;
   an upper mouth piece;
   a frame attached to said upper mouth piece;
   a first fitting attached to said frame, said first fitting being adapted to mate with a second fitting on said nasal mask and to supply air under pressure through said first and second fittings to said nasal mask; and
   said first and second fittings also being adapted such that one fitting can move orbitally with respect to said other fitting while mated therewith.

2. The device of claim 1, wherein said first fitting is tubular and is tapered at the portion that mates with said second fitting.

3. The device of claim 1, wherein said second fitting is tubular and is flared at the portion that mates with said first fitting.

4. The device of claim 1, wherein said first and second fittings form a ball-and-socket joint.

5. The device of claim 1 further comprising a hose for connection to a source of constant positive air pressure connected to said first fitting.

6. The device of claim 5, wherein said frame comprises a support for said hose.

7. The device of claim 6, wherein said frame supports said hose above said mask.

8. The device of claim 1, wherein said nasal mask can move orbitally with respect to said frame.

9. The device of claim 1, wherein said frame comprises a hinge intermediate said upper mouth piece and said first fitting.

10. The device of claim 1, wherein said device further comprises a cushion attached to said frame adjacent said head strap, said cushion being adapted to contact a wearer's forehead.

11. A breathing device comprising:
a nasal mask;
an upper mouth piece;
a frame attached to said upper mouth piece;
a first tubular fitting attached to said frame, said first fitting being adapted to mate with a second tubular fitting on said nasal mask and to supply air under pressure through said first and second fittings to said nasal mask; and
said first fitting being tapered at the portion that mates with said second fitting and said second fitting being flared at the portion that mates with said first fitting.

12. A breathing device comprising:
a nasal mask;
an upper mouth piece;
a frame attached to said upper mouth piece;
a first fitting attached to said frame;
a second fitting attached to said nasal mask, said first and second fitting forming a ball-and-socket joint; and
said first and second fittings being adapted to supply air under pressure to said nasal mask.

13. A breathing device comprising:
a nasal mask;
an upper mouth piece;
a frame attached to said upper mouth piece, wherein said frame is coupled to said nasal mask such that said nasal mask can move orbitally and air under pressure is supplied to said nasal mask through said coupling.

14. A breathing device comprising:
a nasal mask;
an upper mouth piece;
a frame attached to said upper mouth piece; and
a coupling between said frame and said nasal mask adapted to supply air under pressure to said nasal mask and to permit orbital movement of said nasal mask.

15. The device of claim 14, wherein said coupling between said frame and said nasal mask is located at approximately the center of said nasal mask.

16. The device of claim 14, wherein said coupling prevents said nasal mask from moving away from a wearer's face.

17. The device of claim 14, wherein said coupling is made from rigid materials.

18. A method of wearing a device for assisted breathing comprising coupling a nasal mask to a frame attached to an upper mouth piece, wherein said upper mouth piece is operable to be inserted into a user's mouth and said frame contacts said nasal mask such that orbital movement of said mask is possible while air is supplied to said mask through said coupling.

19. The method of claim 18, wherein said frame is retained to a wearer's head at a point remote from said upper mouth piece.

20. A breathing device comprising:
a nasal mask;
an upper mouth piece;
a frame attached to said upper mouth piece;
a first fitting attached to said frame, said first fitting being adapted to mate with a second fitting on said nasal mask and to supply air under pressure through said first and second fittings to said nasal mask;
said first and second fittings also being adapted such that one fitting can move orbitally with respect to said other fitting while mated therewith;
wherein said frame includes a strap attached to said frame for securing the portion of said frame remote from said upper mouth piece to the head of a user.

21. A breathing device comprising:
a nasal mask;
an upper mouth piece;
a frame attached to said upper mouth piece;
a head strap attached to said frame at a portion opposite said upper mouth piece;
a first fitting attached to said frame, said first fitting being adapted to mate with a second fitting on said nasal mask and to supply air under pressure through said first and second fittings to said nasal mask; and
said first and second fittings also being adapted such that one fitting can move orbitally with respect to said other fitting while mated therewith.

22. A breathing device comprising:
a nasal mask;
an upper mouth piece;
a frame attached to said upper mouth piece;
a coupling between said frame and said nasal mask adapted to supply air under pressure to said nasal mask and to permit orbital movement of said nasal mask; and
a strap attached to said frame at a portion opposite said upper mouth piece.

* * * * *